(12) United States Patent
Marchant

(10) Patent No.: US 6,514,535 B2
(45) Date of Patent: *Feb. 4, 2003

(54) BIOADHESIVE HYDROGELS WITH FUNCTIONALIZED DEGRADABLE CROSSLINKS

(75) Inventor: Nancy S. Marchant, Medina, OH (US)

(73) Assignee: Noveon IP Holdings Corp., Cleveland, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/316,688

(22) Filed: May 21, 1999

(65) Prior Publication Data

US 2002/0068087 A1 Jun. 6, 2002

(51) Int. Cl.$^7$ .............................. A61K 9/14; A61K 2/00
(52) U.S. Cl. ....................... 424/486; 424/484; 424/422; 424/489; 424/426
(58) Field of Search ................................ 526/286, 287, 526/288; 424/426, 487, 422, 484, 486

(56) References Cited

U.S. PATENT DOCUMENTS

| | | | | | |
|---|---|---|---|---|---|
| 4,795,436 | A | * | 1/1989 | Robinson | 424/422 |
| 4,898,824 | A | * | 2/1990 | Yip | 435/180 |
| 5,064,495 | A | * | 11/1991 | Omura et al. | 526/288 |
| 5,496,872 | A | * | 3/1996 | Constancis et al. | 523/118 |
| 5,700,848 | A | * | 12/1997 | Soon-Shiong et al. | 424/451 |
| 5,712,356 | A | * | 1/1998 | Bothe et al. | 526/287 |
| 6,297,337 | B1 | * | 10/2001 | Marchant et al. | 526/324 |

* cited by examiner

Primary Examiner—Thurman K. Page
Assistant Examiner—Robert M. Joynes
(74) Attorney, Agent, or Firm—Thoburn T. Dunlap; Hudak, Shunk & Farine Co.

(57) ABSTRACT

This invention relates to A bioadhesive composition comprising two or more essentially excretable, essentially non-degradable polymer backbones, wherein the polymer backbones are crosslinked, said crosslink being degradable in a mammal, said cross-linked bioadhesive composition having an average bioadhesion factor showing bioadhesion equivalent to at least about 100 g s. The concept is to build a hydrogel that demonstrates bioadhesion to a mucosal surface that is crosslinked by a degradable linkage such as disulfide for use inside the body.

15 Claims, No Drawings

BIOADHESIVE HYDROGELS WITH FUNCTIONALIZED DEGRADABLE CROSSLINKS

FIELD OF THE INVENTION

The invention relates to excretable polymer networks that are susceptible to enzymatic cleavage, exchange reactions with mucin, reduction, and oxidation.

BACKGROUND OF THE INVENTION

Hydrogels are polymers that swell in water. They have a large molecular weight that generally cannot be measured by conventional methods because they are too large. Hydrogels are made up of a polymer backbone and crosslinks. Crosslinks can be used to extend the molecular weight of a polymer if the ratio of crosslinker to non crosslinker is low and polymerization is confined below the gel point. Nevertheless if the ratio of crosslinking monomer to non crosslinker monomer is high enough, a gel is formed that swells in a good solvent but does not truly dissolve.

Carbomer resins are high molecular weight, crosslinked, acrylic acid-based polymers. A number of agencies, including the USP-NF, and United States Adopted Names Council (USAN) have adopted the generic name "carbomer" for polyacrylic acid types of resins, exemplified by Carbopol®. Carbopol® resins are water swellable poly(acrylic acids) that are commercially available from the B. F. Goodrich Co. (Specialty Polymers and Chemical Division, Cleveland, Ohio) in several formulations. Polyacrylic acid polymers that are lightly crosslinked with a polyalkenyl polyether are commercially available from B. F. Goodrich under trademarks such as Carbopole® and NOVEON®

Several crosslinked ionic hydrogel materials have been disclosed in the literature. As disclosed by Shah in U.S. Pat. No. 4,693,887, the nature of the crosslinkages in stable or permanent hydrogels is generally of the covalent type, although ionic crosslinkages in polyelectrolyte complexes are also found. Certain block and graft copolymer hydrogels, possessing a hydrophobic-hydrophilic microphase morphology, have been reported by Milkovich (U.S. Pat. No. 4,085,168), Wichterle (U.S. Pat. No. 4,095,877), Nakashima, et al. (*J. Biomed. Materials Res.*, 11, 787 (1977)), and Okano, et al. (*J. Appl. Polymer Sci.*, 22, 369 (1978)). In these hydrogels, the hydrophobic and hydrophilic phases are connected to one another by means of covalent bonds.

A neutral hydrogel of a polymer of ethylene glycol methacrylate or similar monomer crosslinked sufficiently to make the polymer insoluble is disclosed in U.S. Pat. No. 3,551,556. U.S. Pat. No. 3,641,237 discloses hydrogels films prepared by polymerization of lower alkoxy lower alkyl acrylates and methacrylates along with a 0 to 40 percent of a hydrophilic acrylic monomer in the presence of a crosslinking agent. Various monomers are disclosed as useful for the 0 to 40 percent co-monomers, including hydroxyalkyl acrylates and methacrylates, salts of $\alpha,\beta$-unsaturated organic acids and strong acid salts of polymerizable ethylenically unsaturated amine-containing monomers.

For a polymer to be used safely in the body it must be either bio-durable, biodegradable or excretable through the reticuloendothelial system (RES) system. The above mentioned references would be examples of systems that are resistant to degradation by the body. Often resistant materials produce byproducts or lose their material properties in such a manner which give grave concerns to using them in implantable applications. Many of the examples given above would give byproducts that are not easily cleared by the body. It has long been known that the size or Stokes radius of macromolecules is the chief parameter controlling the rate of clearance from the serum compartment by glomerular filtration. Hardwicke, J.; Hulme, B.; Jones, J. H.; Rickets, C. R.; "Measurement of glomerular permeability to polydisperse radioactivity labeled macromolecules in normal rabbits"; *Clin. Sci.* 34, 505 (1968). The term size is used here to descriptively cover both the molecular weight of a polymer sample and also the shape of the polymer molecules. The size filtered by the kidney is generally thought to be 40 angstroms which is often related to the molecular weight of the polymer and viewed as 45,000 Daltons (i.e., 45 kD). Excretability is also a function of the hydrophobicity of the polymer as certain hydrophobic side groups have been shown to lead to deposition in kidney tissue. See for example, Rypacek, F.; Drobnik, J.; Chmelar, V.; Kalal, J.; "The renal excretion and retention of macromolecules, the Chemical structure effect," *Pfluger Arch*, 392, 211 (1982).

The main purpose of this invention is to produce bioadhesive polymeric networks or hydrogels for use in the body while ensuring that the polymeric network or hydrogel will break down into molecular weights that can be cleared by the body. This invention uses a low degradation bioadhesive backbone, synthesized with crosslinks that gel the backbones into a network. This bioadhesive hydrogel can degrade back to a low molecular weight backbone that can be cleared from the body. Thus the matrix is lost via degradation of the crosslinks. This mechanism of degradation may also give different control over the release of materials than that of a matrix, which is degrading via equal scission of the backbone and crosslink junctions.

It has been previously shown that non-ionic, non-bioadhesive electrophoresis hydrogels may be made with disulfide functional crosslinkers. These polyacrylamide electrophoresis gels may be digested to release the material being separated (RNA fragments). See for example, Hansen, H. J., *Anal. Biochem.*, 76, 37 (1976). Electrophoresis, as known to those skilled in the art, uses electrical current and mobility to separate proteins and other such biological compounds in a gel matrix. Therefore, the gel matrix should show little interaction with biological materials and is not considered bioadhesive.

Yip discloses in U.S. Pat. No. 4,898,824 a crosslinked polyacrylamide-sulfhydryl polymer for immobilization of biologically active substances. Saffran, et al. disclose in U.S. Pat. No. 4,663,308 high molecular weight polymers of one or more ethylenically unsaturated monomers copolymerized with a divinylazobenzene compound to coat or otherwise entrap drugs that are labile in the stomach, have an undesirable effect in the stomach, or are targeted at the colon. Release of drug occurs via the cleavage of the azobonds by the azoreductases that abound in the colon but are not prevalent in the stomach or small intestine. U.S. Pat. No. 4,663,308 suggests various acrylic acid esters and amides as well as unsaturated acids as possible monomers. However, the only copolymer exemplified in the patent is a hydroxyethyl-methacrylate (HEMA)-styrene copolymer that contains no ionizable group. This copolymer has low bioadhesion because there are no carboxyl or other ionizable co-monomers. Further, the copolymers of U.S. Pat. No. 4,663,308 are crosslinked under the gel point (branched) and are thus soluble in organic solvents.

Kopecek, et al. disclose in U.S. Pat. No. 5,415,864 colonic-targeted oral drug-dosage forms based on crosslinked hydrogels containing azobonds and exhibiting pH-dependent swelling. These include crosslinked hydrogels that undergo pH-dependent swelling and contain azobonds that are enzymatically cleavable by the azoreductases that reside in the colon; conjugates of hydrogels which exhibit pH-dependent swelling, and optionally include enzymatically-cleavable azobonds, and amino group-containing drugs that are covalently bound to the hydrogel via an aromatic azobond; and a process for making such conjugates. U.S. Pat. No. 5,415,864 does not address the concept of excretable polymer backbones and although the crosslinks are degradable the resulting polymer backbone molecular weight and hydrodynamic radius would be above the limit for renal clearance and the resulting polymer would not be renally cleared from the body.

Schacht, et al. disclose in U.S. Pat. No. 5,407,682 reduction sensitive polymers which are linear macromolecules containing an azo and/or a disulfide bond in their polymer backbone. These are not hydrogel materials and as such will not swell and retain water within the polymeric network. Furthermore, they will not display the bioadhesion properties characteristic of an ionic hydrogel crosslinked via degradable crosslinks.

Kopecek, et al. disclose in U.S. Pat. No. 5,037,883 synthetic polymeric drugs comprising an inert synthetic polymeric carrier combined through a biodegradable spacer with a low molecular weight bioactive molecule Synthesis of these polymeric drugs is also disclosed. U.S. Pat. No. 5,037,883 tries to reduce glomerular filtration and to enhance pinocytosis into target cells. In U.S. Pat. No. 5,037,883, the biodegradable spacer is only susceptible to cleavage after it had been taken into the cell and into the lysosomal compartment. This polymeric drug is designed to be soluble in the bloodstream and is not a hydrogel system. The polymer disclosed in U.S. Pat. No. 5,037,883 is also designed to be inert and is not bioadhesive.

Synthetic polymers based on N-(2-hydroxypropyl) methacrylamide (HPMA) have been proposed as potential drug carriers by Kopacek, et al. in U.S. Pat. No. 4,062,831 and U.S. Pat. No. 4,097,470. Such polymers are freely soluble in aqueous media and have good biocompatibility and little bioadhesion. Furthermore, by the incorporation of p-nitrophenylesters of N-methacrylolyl oligopeptides they can be combined with many drugs which contain a primary amino group.

A temperature sensitive, but not bioadhesive hydrogel of poly N-isopropylacrylamide crosslinked with a small amount of a disulfide containing material has been disclosed by Lee and Park in *Polymer J.* 30, 976–980, (1998). This work created a temperature sensitive hydrogel that was not bioadhesive. This material is temperature sensitive so that at body temperatures this material will be above its lower critical solution temperature (LCST) (approximately 35° C.) and would not be in the hydrogel state. The reduction of the disulfide bonds was attempted with this material, but it is clear that only a small portion of the resultant gel became soluble. Insoluble material was separated from soluble material and only the soluble material was further studied. The molecular weight of the fraction that was not further characterized would be well above the level needed for renal clearance and could not undergo glomerular filtration.

Polymeric drug carriers have been designed to optimize the delivery of therapeutic agents orally (i.e., injestable and/or within the oral cavity), renally (e.g., suppositories), intravenously (i.e., through the bloodstream), ocularly (i.e., in the eyes), nasally (e.g., nasal sprays), vaginally, from surgically implanted polymeric depots, and other known treatment methods.

Polymers for use as bloodstream drug carriers have the criteria of being totally soluble in blood. The polymer may act to enhance the lifetime of the drug in the bloodstream or may help to target the drug to a particular location by including a targeting moiety on the backbone as described in Duncan, R.; "Biological effects of soluble synthetic polymers as drug carriers," *CRC Critical Reviews in Therapeutic Drug Carrier Systems*, 1, 281 (1984). Nevertheless, the polymer/drug conjugate is totally soluble and is initially distributed systemically through the bloodstream. It is also anticipated that the polymeric drug carrier will be internalized into the cell to deliver the drug-polymer conjugate. Cleavage of the drug from the delivery polymer backbone is an important control criteria and extensive work has been conducted to design the drug-polymer linkage so that it is cleaved after internalization into the targeted cell. An added criteria for the polymeric drug carriers is also the general inertness of the carrier polymer. For example, N-2-hydroxypropylmethacrylamide (HPMA) has been widely characterized as a polymeric drug carrier. Carbohydrate side groups have to be added to the HPMA polymer to enhance the polymer's interaction with the cell surface and enhance internalization of the macromolecular conjugate. For example, see Duncan, R.; "Biological effects of soluble synthetic polymers as drug carriers," *CRC Critical Reviews in Therapeutic Drug Carrier Systems*, 1, 281 (1984).

Kopacek, et al. disclose in U.S. Pat. No. 5,037,883 polymeric drug carriers. These polymeric drug carriers reduce glomerular filtration and enhance pinocytosis into target cells. The biodegradable spacer was only susceptible to cleavage after it had been taken into the cell's lysosomal compartment. These polymeric drug carriers are designed to be soluble in the bloodstream and are not bioadhesive hydrogels. As discussed above, U.S. Pat. No. 4,062,831 and U.S. Pat. No. 4,097,470 disclose that the polymeric chains may be cross-linked to a level below the gel point in order to achieve the optimum molecular weight for soluble yet molecular weight extended material and to provide, by the use of biodegradable cross-linkages, a means of degrading the polymer to facilitate elimination from the body. These materials are soluble, but not bioadhesive.

The term "bioadhesion" refers to the ability of some synthetic and biological macromolecules and hydrocolloids to adhere to biological tissues. Bioadhesion systems have been used in dentistry, orthopaedics, ophthalmology. However, there has recently emerged significant interest in the use of bioadhesive materials in other areas, such controlled release systems for local release of bioactive agents. Such applications include systems for release of drugs in the buccal or nasal cavity, and for intestinal or rectal administration. These bioadhesive applications do not require the use of excretable polymer systems as it is generally accepted that the polymeric system will not enter the bloodstream while in this type of application. Nevertheless interest has been building for the use of bioadhesive hydrogels for soft tissue replacement, wound treatments, and depot systems. These applications require more stringent synthesis requirements as described above. In these applications a bioadhesive hydrogel that is excretable is novel and vastly improves the art.

Bioadhesion is a complex phenomenon, depending in part upon the properties of polymers, biological tissue, and the surrounding environment. Several factors have been found to contribute to a polymer's bioadhesive capacity. These factors include the presence of functional groups able to form hydrogen bridges (e.g., —OH, COOH), the presence and strength of anionic charges, sufficient elasticity for the polymeric chains to interpenetrate the mucous layer, and high molecular weight.

Most epithelial surfaces in the body are coated with a mucus membrane. The ability of a material to 'stick' to a mucous membrane is termed mucoadhesion or bioadhesion. Polymers capable of hydrogen bonding are known to be the best at bioadhesion. Crosslinked polyacrylic acid hydrogels such as Carbopol® (B F Goodrich) have some of the best bioadhesion as measured by in vitro testing and have been used in applications where excretability is not important. Internal endothelial surfaces are also coated with a mucus membrane and the ability of an excretable material to 'stick' to an endothelial surface to control and enhance the delivery of pharmaceutical agents, to act as a barrier gel, and yet be cleared from the body is needed.

SUMMARY OF THE INVENTION

This invention relates to the formation of bioadhesive hydrogels that are susceptible to enzymatic cleavage, exchange reactions with mucin, reduction, and oxidation. The concept is to build a hydrogel that demonstrates bioadhesion to a mucosal surface that is crosslinked by a degradable linkage such as disulfide for use inside the body.

DETAILED DESCRIPTION

As used herein, the term "excretable" means refers to glomerular filtration of a hydrodynamic radius of less than 40 Angstroms. As used herein, the term "essentially excretable" means that after cleavage, a major portion of the polymer is excretable. The term "essentially degradable" means that a major portion of degradable crosslinks will degrade while in the body, while the majority of the polymer backbone remains whole.

The term "non-degradable" refers to virtually no further polymer backbone byproducts formed within the time it takes to clear 95% of the polymer backbone from the body. For intraperitonial applications, this time would be at least 24 hours. Applications such as soft tissue replacement after surgery in locations that do not have the flux rate of the intraperitonial cavity could be longer. Intravenous applications could be shorter.

In accordance with the invention, it will be appreciated that "degradable" material is distinct from "cleavable." The term "cleave" means the actual breakage of a polymer backbone into one or more pieces. In degradation, the polymer backbone may be damaged while not breaking the backbone into smaller pieces.

The invention relates to a bioadhesive composition having two or more essentially excretable, essentially non-degradable polymer backbones, wherein the polymer backbones are crosslinked, the crosslink being degradable in a mammal, the cross-linked bioadhesive composition showing bioadhesion equivalent to at least about 100 gram second (g s). Gram second are the units in which bioadhesion is measured. It is a unit of force—it takes at least this much force to break the adhesive bond.

The invention also relates to a bioadhesive composition wherein the polymer backbone comprises at least one of a homopolymer, copolymer, terpolymer, or interpolymer hydrogel selected from the group consisting of polycarboxylic acids, or salts thereof, and vinyl polymerizable monomers as long as the polymeric backbone has a hydrodynamic radius of 40 Angstroms or less.

The invention also relates to a crosslinked ionic polymer wherein the carboxylic acid is selected from the group consisting of acrylic acids, methacrylic acids, and maleic acids.

The invention also relates to a bioadhesive composition wherein the carboxylic acid polymer backbone comprises at least one carboxylic acid monomer with a neutral but hydrophilic co-polymerizable monomer.

The invention also relates to a bioadhesive composition wherein the vinyl polymerizable monomer comprises at least one of a vinyl or vinylidene monomer, wherein the monomer has at least one terminal $CH_2=C$ group.

The invention also relates to a bioadhesive composition wherein the polymer comprises at least one $C_1$–$C_5$ alkyl vinyl ether polymerized therein.

The invention also relates to a bioadhesive composition wherein the polymer comprises at least one $C_2$–$C_{30}$ α-olefin polymerized therein.

The invention also relates to a bioadhesive composition further having at least one monomer of the formula:

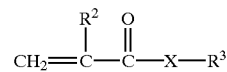

wherein $R^2$ is hydrogen, methyl or ethyl, X is O or NH, and $R^3$ is alkyl of 1 to 30 carbon atoms, and in an amount of less than 50 weight percent based upon the weight of the crosslinked ionic polymer backbone.

The invention also relates to a bioadhesive composition wherein $R^2$ is hydrogen or methyl and $R^3$ is an alkyl group containing 2 to 20 carbon atoms.

The invention also relates to a bioadhesive composition synthesized by at least one of precipitation or dispersion polymerization in an organic media.

The invention also relates to a bioadhesive composition synthesized by reverse emulsion polymerization.

The invention also relates to a bioadhesive composition wherein the polymer backbone comprises at least one hydrophilic, hydrophobic, or cationic subunit.

The invention also relates to a bioadhesive composition, wherein the polymer backbone is crosslinked to at least one pharmaceutically active agent, the crosslink being degradable in a mammal.

The invention also relates to a bioadhesive composition wherein the essentially excretable polymer backbone has a hydrodynamic radius of less than about 40 Angstroms.

The invention also relates to a bioadhesive composition, wherein the crosslink is at least one member selected from the group consisting of disulfides, esters, peptides, and thiols.

The invention also relates to a bioadhesive composition, wherein the polymer backbone is cationic and the crosslink is a disulfide crosslink.

The invention also relates to a bioadhesive composition, wherein the polymer backbone comprises a side chain further comprising a cationic primary amine and the crosslink is attached to the primary amine.

The invention also relates to a bioadhesive composition, wherein the polymer backbone comprises at least one subunit selected from the group consisting of maleic anhydrides and vinyl ethers.

The invention also relates to a bioadhesive composition wherein the polymer backbone comprises subunits selected from the group consisting of polyacrylic acids, polymethacrylic acids, allyl, allyl amines, acrylic acid esters, amides, pH-sensitive monomers, N-vinyl pyrrolidones, hydroxyethylmethacrylates (HEMA), and combinations thereof.

The invention also relates to a bioadhesive composition, wherein the bioadhesive is ionic.

The invention also relates to a bioadhesive composition, wherein the polymer backbone is at least one member selected from the group consisting of a polyacrylic acid, a methacrylic acid, an allyl amine, acryl amine, and combinations thereof.

The invention also relates to a method of making a bioadhesive composition having two or more essentially excretable, essentially non-degradable polymer backbones, wherein the polymer backbones are crosslinked, the crosslink being degradable in a mammal and the cross-linked bioadhesive composition showing bioadhesion equivalent to at least about 100 g s, the method having the steps of:

a) dissolving the polymer in a suitable solvent, b) reacting with the crosslinking agent, and c) isolating the crosslinked composition.

The invention also relates to a bioadhesive composition further having at least one pharmaceutical agent.

The invention also relates to a bioadhesive composition having two or more essentially excretable, essentially non-degradable polymer backbones, wherein the polymer backbones are crosslinked, the crosslink being degradable in a mammal and the cross-linked bioadhesive composition having an average bioadhesion factor showing bioadhesion equivalent to at least about 100 g s; produced by the steps of:

a) combining the monomer and co-polymerizable degradable crosslinker, b) conducting the polymerization, and c) Isolating the crosslinked bioadhesive excretable system.

The invention also relates to an implantable barrier device having the bioadhesive composition.

The invention also relates to a coating for a medical device having the bioadhesive composition.

The invention also relates to a method of treating bone disease, having contacting the bioadhesive composition with bone.

The invention also relates to an excretable reaction product resulting from the biological breakdown of the bioadhesive hydrogel.

The invention also relates to a method of treating cancer, comprising administering to a mammal an effective amount of the bioadhesive composition.

The invention also relates to a method wherein the bioadhesive composition further comprises a pharmaceutical agent.

The invention also relates to a method of treating a surgical cavity, comprising administering to a patient an effective amount of a bioadhesive composition further having a bioactive agent or component.

The invention also relates to a method of reducing host rejection of a medical device or implant having administering to a mammal a bioadhesive composition.

The invention also relates to a method of reducing host rejection of a medical device or implant having administering to a mammal a bioadhesive composition further having a bioactive agent or component.

This invention relates to the formation of networks that are susceptible to enzymatic cleavage, exchange reactions with mucin, reduction, and oxidation. One method to produce polymers for use in the body is to ensure that they will break down into molecular weights that can be cleared by the body. With a low degradation backbone, one method is to synthesize a system that has crosslinks that extend the network and degrade back to a low molecular weight backbone that can be cleared from the body. Thus the matrix is lost via degradation of the crosslinks. This mechanism of degradation may also give different control over the release of materials than that of a matrix, which is degrading via equal scission of the backbone and crosslink junctions.

Carbomer like polymer systems with disulfide based crosslinkers and controlled molecular weight backbones would create a crosslink degradable and excretable system. Other hydrogel matrices by using other hydrophilic monomers may also be produced as long as the hydrogel formed is bioadhesive. Bis N,N'-acrylamide cystamine (Bis [acrylamidoethyl]disulfide) has been documented as being useful in forming reversible crosslinked electrophoresis gels. Alternatively the amino acid cysteine and the disulfide version cystine may be acryloated other thiol/disulfide combinations can be used as long as there is a polymerizable functionality attached (e.g., acryl or allyl). Controlled molecular weight backbones may be synthesized by one skilled in the art by including free radical transfer agents, or conducting the polymerization in such a manner that the degree of polymerization is limited to the excretable range.

Degradable links are mostly used as crosslinks within the polymer network, but may also link to pharmaceutical agents or biological membranes. The term "crosslink" in this invention also covers other these other uses of degradable links.

This invention will result in new formulation and application opportunities where degradable crosslinking schemes are beneficial such as controlled release formulations for pharmaceutical or agricultural application. This release may be achieved through both diffusion and degradative processes in the gel.

Disulfide bonds crosslink two portions of the polymer network. This form of sulfur is relatively stable but can be reduced to the sulfhydryl group thus breaking the crosslink. It may also be oxidized to break the crosslink by forming sulfonic acid or sulfate salts, thus breaking the crosslink. Alternatively the sufhydryl group may be oxidized to form disulfide crosslinks. Polymers may be made using either a disulfide based monomer system or a thiol based monomer system. For example, in a low molecular weight hydrophilic polymer with thiol groups, the thiol group is oxidized to give a crosslinked gel. It may be envisioned that drug may be distributed through a low viscosity system which is then crosslinked.

Brookfield viscosity is a commonly used term for measuring the viscosity of plastisols and other liquids of a viscoelastic nature. Brookfield viscosity is determined by measuring the shearing stress on a spindle rotating at a definite, constant speed while it is immersed in the sample. Brookfield viscosity is measured in centipoises or mPa sec. Viscosity is a function of shear rate and is defined as shear stress/shear rate.

A crosslinked gel may be made using a disulfide crosslinker. It may be eroded through gradual reduction or oxidation of the crosslinks. One major power of the disulfide system is that it undergoes exchange reactions. A free thiol may exchange into a disulfide bond and cause rearrangement. This may be used in bioadhesive applications where binding to mucin disulfide bonds or externally available thiols and disulfides of proteins may be exchanged.

Any thiol containing reagents such as dithiothreitol, dithioerythritol, 2 mercaptoethanol and mercaptoethylamine, and cysteine can serve as reducing agents for disulfides. Complete conversion of disulfide to thiol can be achieved with excess reducing agents. With Dithiothreitol, low level is enough to drive the reaction to completion because of the thermodynamically favored formation of a 6 membered ring product. In protein chemistry, the mild reagents will generally reduce only the exposed disulfide bonds but not those buried inside the protein. Therefore one could see that a gradual erosion of disulfide bonds would occur with a carbomer like matrix. The apparent pH of the mixture will also influence the ability to exchange the disulfide to sulfhydryl. The colon is known to be a reducing environment and there may be a different rate of reduction/oxidation depending upon the location in the body.

In order to re-establish a disulfide crosslink, the sulfhydryl bond is oxidized to the disulfide. Any oxidizing agent such as air, iodide or hydrogen peroxide, is capable of oxidizing the sufhydryl group.

One could also envision making a system with a sulfhydryl as a method to bind an active drug by forming a disulfide that is released upon reduction, or forming a sulfate upon oxidation.

To ensure eventual clearance from the body, the hydrogel is made up of polymeric backbones of molecular weight below renal clearance (45 kD) crosslinked by degradable links. The degradable links in the preferred embodiment are disulfide links. However, several types of links are known to be degradable.

Other useful types of degradable links include:
1. Esters: Esters which are subject to hydrolysis
2. Peptide: Certain peptide linkages are subject to enzymatic degradation, length and peptide sequence determines the rate and likelihood of cleavage.
3. Disulfide: Cleaved by reducing agents and enzymatic reduction to thiols
4. Diol: (e.g., disuccinimidyl tartrate) cleaved by oxidizing environments (e.g., macrophages)

The rate of cleavage of the crosslinks may be controlled based on the application and can be varied. A tightly crosslinked hydrogel is slower to degrade than a loosely crosslinked gel. This is due in part to accessibility of the crosslinks. Those that require interaction with an enzyme for degradation have steric hindrance of the backbone that interferes with the enzyme reaching the link to be degraded. The term "loosely crosslinked" means a low ratio of crosslinks to polymer backbone. The present invention may contain more than one type of crosslink to control the rate and mechanism of hydrogel degradation and drug release.

The nomenclature "two or more backbones" as used herein refers to two or more chains and not two or more types. One type of backbone can be used or several types of backbones can be crosslinked together. Furthermore, backbones can have one type of subunit or multiple types of subunits (e.g., co-polymers), or may be branched.

There are two methods to make the polymer. The first method is to polymerize monofunctional monomers with the multifunctional monomer containing the degradable section. For example, acrylic acid is copolymerized with bis acrylamido cystamine (BAC) using a free radical polymerization.

The second method is to take a preformed polymer and react it with a crosslinking agent. For example, polyacrylic acid is reacted with cystine and coupled using carbodiimide assisted amide link formation. In another example, polymer with an amine functional monomer is crosslinked by reaction with dithiobis[succinimidyl propionate] which will selectively react with the amine functional monomer.

The following crosslinking monomers are typically used in the present invention: dithiols: 3-[(2-aminoethyl)dithio] propionic acid-HCl—will react with an amine on one and a carboxylic acid on the other, bis-[beta-(4-azidosalicylamido) ethyl]disulfide-photoreactive phenylazides, dithiobis [succinimidyl propionate] (Lomant's reagent)—reactive succinimide will react with amines, cystamine, cystine, and homocystine—reactive coupling with carboxylic acids, dimethyl 3,3'-dithiobispropionimidate—2-HCl reactive toward amine groups, 3,3'dithiobis[sulfosuccinimidyl propionate] water soluble version of Lomant's reagent, ethylene glycol bis[succinimidyl succinate] and ethylene glycol bis [sulfosuccinimidyl succinate]—hydrolysis of ester groups, reactive toward amine functionality, (N-succinimidyl [4-azidophenyl] 1,2'-dithiopropionate)—photoreactive and reactive toward amine, (sulfosuccinimidyl[4-azidophenyidithio] propionate)—water soluble, photoreactive and reactive toward amine dithiolglycolic acid and oxidized glutathione—reactive toward amines with carbodiimide assisted coupling, any $H_2N-R-S-S-R'-NH_2$— reactive toward carboxylic acids with carbodiimide coupling.

A hydrogel with a disulfide cross linker can be synthesized from polyacrylic acid in the presence of a crosslinker which has disulfide incorporated to make a crosslinked polymer with disulfide bonds. Such a hydrogel can be active as a bioadhesive, mucoadhesive, metalloprotease (MMP) inhibitor, and in many other applications as shown by following examples of pharmaceutical agents.

Hydrophobic, hydrophilic, anionic, cationic, and neutral monomers can be used as copolymers with polyacrylic acid get a hydrogel with swellability in water. Either the polymer is active itself or can bind an active agent (e.g., pharmaceutical agent). The disulfide bonds can break at a cell membrane, or other part of a mammal's body. The active agent is released as the polymer fragments. The active agent may be quickly available or can also be designed to take a long time to affect the body. After releasing active agent or directly affecting the body, the cleaved hydrogel is cleared by the body. The hydrogel can be designed to directly affect the body before, during, and/or after fragmentation. The polymer must be cleared by kidney if used in body areas that are cleansed into the kidney. 40 Angstroms or less is clearable by the kidney. In this invention's preferred embodiment, the cleaved hydrogel is cleared renally. It is understood that the cleaved hydrogel may also at least partially be cleared from the body by non-renal mechanisms. For example, a small percent of the cleaved hydrogel may enter the bile.

Pharmaceutical agents can be physically trapped within the hydrogel, can be chemically attached to the hydrogel by crosslinking agents, or can hydrogen bond to the hydrogel, or any combination of physical and chemical attachment.

Active stereospecific thiol compounds may be bound to the present polymers via disulfide bonds. A polymer with thiol side groups can be used to deliver these active thiol containing therapeutics. The thiol therapeutic and polymer may be oxidized to form a disulfide link. This may then be reduced via reaction with the body such as the thioredoxin system, glutathione, and other sulfide reducing systems of the body. Such linking methods are known. See for example, *J. Med. Chem.*, 36:4030 (1993); U.S. Pat. No. 5,852,213; U.S. Pat. No. 4,595,700; as well as WO/9407481; WO/9513289; and WO/9509833.

To reversibly bind a thiol-containing compound to a carboxylic acid functional polymer, one method that can be used is to form a thiol ester bond. This is achieved by converting a portion of the carboxylic acid side groups to acyl halides using techniques known in the art. The polymer-containing acyl halide will then react with thiol-containing compounds to form the thiol ester. The thiol ester group can then undergo hydrolysis to regenerate the thiol containing compound and the carboxylic acid functionalized polymer.

U.S. Pat. No. 5,849,951 describes typical hydroxamic acid inhibitor synthesis using solid support. The functional groups in the polystyrene solid support, for example, can be incorporated as a small co-monomer amount in the instant polymers. The contents of this patent are hereby incorporated by reference.

Polymers which present hydroxyl groups as the points of attachment for the compound may be used as derivatives of benzyl alcohol, the peptide, or non-peptide being attached as a benzyl ester and cleaved by hydrolysis, acidolysis or aminolysis to release the compound as a carboxylic acid, or as a carboxamide. Also suitable are polymer substrates which present amino groups, including derivatives of piphenylmethylamine, the peptide or non-peptide being attached as a carboxamide and cleaved by acidolysis to release the peptide or non peptide as a carboxamide. Substitution of such linkers by a nitro group enables the photolytic cleavage of the peptide or non peptide from the residue of the solid substrate.

The polymers in accordance with the invention may be bound to an active compound which is directly or indirectly linked to the relevant N or O atom by a covalent bond which is cleavable by acid hydrolysis. Within carboxylic acid polymers, a small amount of the amine substituted monomer or hydroxyl substituted monomer can be copolymerized or generated through methods known in the art of solid phase peptide synthesis. Known base substrates also include amino- and hydroxy- functionalized solid substrates, i.e., those which are chemically modified by introduction of amino or hydroxyl groups, to serve as convenient points for further chemical manipulation.

It is known in the art of solid phase peptide synthesis that hydroxyl- or amino-carrying linker groups can be introduced onto amino and hydroxy functionalized solid substrates, the linker group having characteristics which facilitate the cleavage of the desired synthesized molecule from the solid support. Thus, for hydroxyl-carrying linker groups, the first amino acid of the peptide to be constructed can be attached as an ester formed between the linker-presented hydroxyl group and the carboxyl group of the amino acid. For amino-carrying linker groups, the first amino acid of the peptide can be attached as a carboxamide formed between the linker-presented amino group and the carboxyl group of the amino acid. An example of a solid support resin presenting amino groups on linker groups attached to the base substrate is the resin 5-(4'-aminomethyl-3',5'-dimethoxyphenoxy)-(N,4-methyl benzhydryl)-pentyramide copolymer. Protecting groups can be employed during the synthesis to protect hydroxyl groups, amine groups carboxyl protecting group. However, the product containing the protecting groups can be further treated, in one or several steps, before or after isolation from the reaction medium, to remove any amine protecting group, carboxyl protecting group or hydroxyl protecting group present. Removal of amine protecting groups, carboxyl protecting groups or hydroxyl protecting groups is known. For example, see T. W. Greene, *Protective Groups in Organic Synthesis,* 2nd Edition, (New York, 1991). Active compounds of the hydroxamic acid family can also be bound to the polymer through an hydroxamate ester. Through hydrogenation, the hydroxamic acid is liberated from the polymers. Reaction of a polymer containing styrene with $CH_2Cl$ side group is then converted to an o-benzyl hydroylamine side group through known techniques. This functional precursor is then bound to a stereospecific carboxylic acid, or ester or acyl chloride through conventional peptide coupling conditions to link the stereospecific hydroxamate to the polymeric support. Through hydrolysis reactions in the body, the free hydroxamic acid is generated. Compounds and active inhibitors in this regards are described in e.g., U.S. Pat. Nos. 5,830,915; 5,773,428; 5,872,152; 5,849,951; 5,840,939; 5,763,621; 5,747,514; 5,700,838; 5,691,382; and 5,652,262. The contents of these patents are hereby incorporated by reference.

A number of additional pharmaceutical agents can be used in accordance with the invention. Suitable types of pharmaceutical agents include, for example, polynucleotides, oligonucleotides, peptides (such as oligopeptides and polypeptides) including cytokines, proteins, enzymes, hormones, monoclonal antibodies, human growth hormones, clotting factors, colony stimulating factors, erythropoietins, tissue plasminogen activators, recombinant soluble receptors, and vaccines.

Preferred pharmaceutical agents include cytokines, antibacterial agents, anti-neoplastic agents, anti-fungal agents, immunomodulators, antiparasitic agents, and CNS agents. Preferred pharmaceutical agents thus include taxane-related antineoplastic agents such as paclitaxel (Taxol®), anthracyclines (including doxorubicin, daunorubicin, epirubicin, idarubicin, mithoxanthrone and carminomycin), mitomycin-type antibiotics, polyene antifungals such as amphotericin B, immunomodulators including tumor necrosis factor alpha (TNFα), and interferons.

Suitable preferred agents include antibacterial agents such as penicillin-related compounds including 9-lactam antibiotics, broad spectrum penicillins, and penicillinase-resistant penicillins (such as ampicillin, ampicillin-sublactam, nafcillin, amoxicillin, cloxacillin, methicillin, oxacillin, dicloxacillin, azocillin, bacampicillin, cyclacillin, carbenicillin, carbenicillin indanyl, mezlocillin, penicillin G, penicillin V, ticarcillin, piperacillin, aztreonam and imipenem, cephalosporins (cephalosporins include first generation cephalosporins such as cephapirin, cefaxolin, cephalexin, cephradine and cefadroxil; second generation cephalosporins such as cefamandole, cefoxitin, cefaclor, cefuroxime, cefuroxime axetil, cefonicid, cefotetan and ceforanide; third generation cephalosporins such as cefotaxime, ceftizoxime, ceftriaxone, cefoperazone and ceftazidime), tetracyclines (such as demeclocytetracycline, doxycycline, methacycline, minocycline and oxytetracycline), beta-lactamase inhibitors (such as clavulanic acid), aminoglycosides (such as amikacin, gentamicin C, kanamycin A, neomycin B, netilmicin, streptomycin and tobramycin), chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides (such as sulfanilamide, sulfamethoxazole, sulfacetamide, sulfadiazine, and sulfisoxazole), trimethoprim-sulfamethoxazole, quinolones (such as nalidixic acid, cinoxacin, norfloxacin and ciprofloxacin), methenamine, nitrofurantoin and phenazopyridine. Such agents further include agents active against protozoal infections such as chloroquine, diloxanide furoate, emetine or dehydroemetine, 8-hydroxyquinolines, metronidazole, quinacrine, melarsoprol, nifurtimox, pentamidine, sodium stibogluconate and suramin.

Suitable pharmaceutical agents also include antifungal agents such as amphotericin-B, flucytosine, ketoconazole, miconazole, itraconazole, griseofulvin, clotrimazole, econazole, terconazole, butoconazole, ciclopirox olamine, haloprogin, toinaftate, naftifine, nystatin, natamycin, undecylenic acid, benzoic acid, salicylic acid, propionic acid and caprylic acid. Suitable agents further include antiviral agents such as zidovudine, acyclovir, ganciclovir, vidarabine, idoxuridine, trifluridine, foxcarnet, amantadine, rimantadine, and ribavirin.

The polymer compositions can further comprise a variety of polypeptides including antibodies, immunomodulators or cytokines (including interferons or interleukins), peptide hormones (such as colony stimulating factors and tumor necrosis factors), hormone receptors, neuropeptides, lipoproteins (such as α-lipoprotein), erythropoietins, growth hormones, thyroid hormones, toxins such as diphtheria toxin, proteoglycans such as hyaluronic acid, and glycoproteins such as gonadotropin hormone.

The polymers also can be administered in conjunction with enzyme inhibiting agents such as reverse transcriptase inhibitors, protease inhibitors, angiotensin converting enzymes, 5α-reductase, and the like. Typical agents include peptide and nonpeptide agents including finasteride, lisinopril, saquinavir, quinapril, ramipril, indinavir, ritonavir, nelfinavir, zalcitabine, zidovudine, allophenylnorstatine, kynostatin, delaviridine, bis-tetrahydrofuran ligands, and didanosine.

It will be appreciated that combinations of these agents can also be employed. It will be further appreciated that the invention is not directed to the underlying specific activity of these agents, but rather to the compositions themselves.

Chemotherapeutic agents appropriate for use in the invention also include, vinca alkaloids (such as vincristine and vinblastine), mitomycin-type antibiotics (such as mitomycin-C and N-methyl mitomycin-C), bleomycin-type antibiotics such as bleomycin A2, antifolates such as methotrexate, aminopterin, and dideaza-tetrahydrofolic acid, colchicine, demecoline, etoposide, taxanes such as paclitaxel (Taxol®), and anthracycline antibiotics. Suitable tetracycline antibiotics include, without limitation, doxorubicin, daunorubicin, carminomycin, epirubicin, idarubicin, mithoxanthrone, 4-demethoxy-daunomycin, 11-deoxydaunorubicin, 13-deoxydaunorubicin, adriamycin-14-benzoate, adriamycin-14-octanoate, or adriamycin-14-naphthaleneacetate.

The appropriate dosage for the pharmaceutical agents will often be about comparable to that of the pharmaceutical agent alone; dosages will be set by the prescribing medical professional considering many factors including age, weight, and condition of the patient, as well as the pharmacokinetics of the specific agent. Often the amount of agent required for effective treatment will be less than the amount required using the free pharmaceutical agent. Generally, an effective amount of pharmaceutical agents is that amount effective to reduce the symptoms of the disease sought to be treated, or to induce a pharmacological change relevant to treating the disease sought to be treated.

The foregoing detailed description is given for clearness of understanding only, and no unnecessary limitations should be understood therefrom. Hence, numerous modifications and changes can be made by those skilled in the art without departing from the spirit and scope of the invention.

The following examples will serve to further typify the nature of this invention but should not be construed as a limitation in the scope thereof, which scope is defined solely by the appended claims.

EXAMPLE 1

Free Radical Polymerization of Monomer and Crosslinker

Synthesis. 1335 mL of ethyl acetate was introduced into a two liter water jacketed reactor. 165 grams acrylic acid (100 parts) and 0.33 gram bis acrylamide cystaime (0.2 parts per hundred monomer) and 1.5 parts of potassium carbonate ($K_2CO_3$) were added. The reactor was brought to temperature, 45° C. and di-(2-ethylhexyl) peroxydicarbonate 0.248 gram (0.15 parts) was added. The reaction was held at temperature for 5 hours. Lubrizol 243 (0.246 gram, 0.15 parts) was added and the reaction was run for two more hours. The reaction was cooled to room temperature and transferred to a rotary evaporator flask and dried overnight. The product was isolated as a white powder.

Viscosity measurements. A known wt % polymer was dispersed in deionized water as shown in the following table. The viscosity was measured using a Brookfield viscometer at 20 rpm using the correct spindle as directed by the test. Brookfield viscosity was correlated to the level of crosslinking of the sample and the efficiency of the gel in thickening deionized water. The polymer was neutralized to pH 7.5 using sodium hydroxide (NaOH). The viscosity was then measured.

Dispersion viscosity of the sample as dispersed in deionized water and not neutralized was measured for 0.2 wt %, polymer in 400 mL water, 0.5 wt % polymer in 400 mL water, and 1.0 wt % polymer in 400 mL water.

|  | AA | MAA | BAC (phm) | 0.2 wt % B.V. | 0.5 wt % B.V. | 1.0 wt % B.V. |
| --- | --- | --- | --- | --- | --- | --- |
| Polymer 1 | 100 | 0 | 0.2 | 286 | 650 | 1080 |
| Polymer 2 | 100 | 0 | 0.4 | 700 | 1440 | 2550 |
| Polymer 3 | 100 | 0 | 0.6 | 970 | 2480 | 4070 |
| Polymer 4 | 50 | 50 | 0.4 | 434 | 980 | 1480 |
| Polymer 5 | 50 | 50 | 0.6 | 575 | 2690 | 4800 |
| Polymer 6 | 100 | 0 | 0.8 | 1090 | 3510 | 6600 |
| Polymer 7 | 100 | 0 | 1.0 | 820 | 3180 | 6450 |
| Polymer 8 | 100 | 0 | 1.2 | 820 | 3670 | 8950 |

B.V. Brookfield viscometer
phm: parts per hundred monomer
*AA: Acrylic Acid
*MAA: Methacrylic acid
*BAC: bis acrylamido cystamine

EXAMPLE 2

Synthesis. To a mechanically stirred flask a solution of 40 wt % polyacrylic acid was added. The solution was warmed to 50° C. The pH was adjusted to 8.3 with NaOH. Cystamine was added to the flask and then 20 minutes later 1-ethyl-3-3-dimethylaminopropyl)carbodiimide hydrochloride (EDC) was added. The solution immediately thickened and stirring was stopped. The polymer was removed from the flask and washed with isopropyl alcohol and acetone. The polymer was ground and dried in a vacuum oven until it formed a flowable powder. The Table below shows a series of polymers synthesized in this manner. The starting molecular weight of the polyacrylic acid was 30,000 Daltons.

|  | Polymer solution gm | Cystamine gm | EDC gm | Polymer yield gm |
| --- | --- | --- | --- | --- |
| Polymer 9 | 82.47 | 0.782 | 2.6623 | 25.53 |
| Polymer 10 | 82.47 | 1.564 | 5.3246 | 24.67 |
| Polymer 11 | 82.47 | 0.196 | 0.6656 | 26.21 |
| Polymer 12 | 82.47 | 0.391 | 1.3312 | 25.33 |

EXAMPLE 3

Reduction of Disulfide Crosslinked Gel

Polymer gel formed in example 2 was suspended in distilled water. Dithioltheritol was added to the solution in a 1:1 molar ratio to the cystamine. Immediate reduction in viscosity was observed and the polymer sample was dialyzed for 3 days and then freeze dried. Thiol contents of the polymers were checked via Ellman's Assay and GPC molecular weight (F) taken on the recovered solids. The GPC showed bimodal distribution with a high molecular weight component and a low molecular weight component due to incomplete reduction of the disulfide groups.

|  | Thiol content Mol % | Mw | Mn | MWD |
|---|---|---|---|---|
| Polymer 9 | 0.76 | 104,800 | 10420 | 10.0597 |
| Polymer 10 | 1.52 | 84430 | 10970 | 7.6937 |

EXAMPLE 4

Synthesis. To a mechanically stirred flask a solution of 30 wt % polymethacrylic acid was added. The solution was warmed to 50° C. The pH was adjusted to 8.3 with NaOH. Cystamine was added to the flask and then 20 minutes later 1-ethyl-3-3-dimethylaminopropyl)carbodiimide Hydrochloride (EDC) was added. The solution was monitored for an increase in viscosity. Polymer was removed from the flask and precipitated with isopropyl alcohol and acetone. The polymer was ground and dried in a vacuum oven until it formed a flowable powder. The Table below shows a series of polymers synthesized in this manner. The starting molecular weight of the poly methacrylic acid was 30,000 Daltons.

|  | Polymer solution gm | Cystamine gm | EDC gm | Swell properties | Polymer yield gm |
|---|---|---|---|---|---|
| Polymer 13 | 100 | 0.79 | 1.575 | 170 gm H$_2$O/gm Poly | 45.05 |
| Polymer 14 | 100 | 0.39 | 0.787 | higher viscosity | 44.85 |
| Polymer 15 | 100 | 1.58 | 3.15 | particulate | 43 |

EXAMPLE 5

Reduction of Disulfide Crosslinked Gel

Polymer 15 formed in example was suspended in distilled water. Dithiolthreitol was added to the solution in a 1:1 molar ratio to the cystamine. Immediate reduction in swollen particle size and viscosity was observed. The polymer sample was dialyzed for 3 days and then freeze dried. Thiol content of the polymers were checked via Ellman's Assay and GPC Mw taken on the recovered solids.

|  | Thiol content Mol % | Mw × 10$^{-3}$ | Mn × 10$^3$ | MWD |
|---|---|---|---|---|
| Polymer 15 | 0.98 | 27.1 | 8.57 | 3.16 |
| PolyMAA starting material | 0 | 22.9 | 4.67 | 4.90 |

EXAMPLE 6

Synthesis. To a mechanically stirred flask a solution of 25 wt % polyacrylic acid was added. The solution was warmed to 50° C. The pH was adjusted to 8.3 with NaOH. Cystine was added to the flask and then 20 minutes later 1-ethyl-3-3-dimethylaminopropyl)carbodiimide Hydrochloride (EDC) was added. The solution was monitored for an increase in viscosity. Polymer was removed from the flask and precipitated with isopropyl alcohol and acetone. The polymer was ground and dried in a room temperature vacuum oven until it formed a flowable powder. The Table below shows a series of polymers synthesized in this manner. The starting molecular weight of the polyacrylic acid was approximately 370,000 Daltons.

|  | Polymer solution gm | Cystine gm | EDC gm | Swell properties | Polymer yield gm |
|---|---|---|---|---|---|
| Polymer 16 | 100 | 0.79 | 1.575 | 270 gm H2O/gm poly | 39.3 |
| Polymer 17 | 100 | 0.39 | 0.787 | Increased viscosity | 39.68 |
| Polymer 18 | 100 | 1.58 | 3.15 | 160 gm H2O/gm poly | 42.05 |

EXAMPLE 7

Reduction of Disulfide Crosslinked Gel

Polymer 15 formed in example was suspended in distilled water. Dithiolthreitol was added to the solution in a 1:1 molar ratio to the cystamine. Immediate reduction in swollen particle size and viscosity was observed. The polymer sample was dialyzed for 3 days and then freeze dried. Thiol content of the polymers were checked via Ellman's Assay and GPC Mw taken on the recovered solids.

|  | Thiol content Mol % | Mw × 10$^{-3}$ | Mn × 10$^3$ | MWD |
|---|---|---|---|---|
| Polymer 18 | 0.53 | 251 | 30.9 | 8.12 |
| PolyAA starting material | 0 | 362 | 52.5 | 6.89 |

EXAMPLE 8

Synthesis. To a mechanically stirred flask a solution of 25 wt % polyacrylic acid was added. The solution was warmed to 50° C. The pH was adjusted to 8.3 with NaOH. Cystine was added to the flask and then 20 minutes later 1-ethyl-3-3-dimethylaminopropyl)carbodiimide Hydrochloride (EDC) was added. The solution was monitored for an increase in viscosity. Polymer was removed from the flask and precipitated with isopropyl alcohol and acetone. The polymer was ground and dried in a room temperature vacuum oven until it flowed as a powder. The Table below shows a series of polymers synthesized in this manner. The starting molecular weight of the polyacrylic acid was approximately 6,000 Daltons.

|  | Polymer solution gm | Cystine gm | EDC gm | Swell properties | Polymer yield gm |
|---|---|---|---|---|---|
| Polymer 19 | 50.51 | 1.68 | 3.34 | Swollen particulate | 36.68 |

-continued

| | Polymer solution gm | Cystine gm | EDC gm | Swell properties | Polymer yield gm |
|---|---|---|---|---|---|
| Polymer 20 | 22.76 | 1.46[a] | 5 | Thickened | 19.23 |
| Polymer 21 | 14.85 | 1.46[a] | 5 | Swollen particulate | 10.2 |

[a]cystamine

EXAMPLE 9

Reduction of Disulfide Crosslinked Gel

Polymer 19,20,21 formed in example were suspended in distilled water. Dithiolthreitol was added to the solution in a 1:1 molar ratio to the disulfide compound. Immediate reduction in swollen particle size and viscosity was observed. The polymer sample was dialyzed for 3 days and then freeze dried. Thiol content of the polymers were checked via Ellman's Assay and GPC Mw taken on the recovered solids.

| | Thiol content Mol % | $Mw \times 10^{-3}$ | $Mn \times 10^3$ | MWD |
|---|---|---|---|---|
| Polymer 19 | <1% | 6.26 | 2.33 | 2.69 |
| Polymer 20 | 4.462 | 6.1 | 2.19 | 2.79 |
| Polymer 21 | 7.943 | 6.09 | 1.96 | 3.11 |
| PolyAA starting material | 0 | 6.08 | 2.25 | 2.70 |

EXAMPLE 10

Synthesis of Thiol Substituted Polymer That Can be Oxidized to Crosslinked Polymer In a 50 ml vial 12.5 of polyallylamine was suspended as a 20 wt % solution. The solution was previously purged with nitrogen for 30 minutes. The Mw of the polymer was 17,000. The degree of polymerization was 298. The pH was adjusted until the final pH was 9.4. 2 Iminothiolane (0.08138 gm) was added. The polymer was acidified and precipitated with isopropanol. The yield was 5.1 gm. The product was labeled Polymer 22.

EXAMPLE 11

Synthesis of a Cationic Charged Hydrogel With Disulfide Crosslinks

In a 50 ml vial suspend 12.5 ml of polyallylamine polymer of Mw 17,000 Daltons as a 20 wt % solution. Crosslinking reagent was added to the solution. The disulfide containing agent was diothiobis (succinimidyl propionate). Lomant's reagent was dissolved in 5 ml DMF. Polymer was isolated by ionizing with HCl and precipitated in isopropanol. Yield was 2 gm and labeled Polymer 23.

EXAMPLE 12

Oxidation of Thiol Containing Polymers

Polymer 10 was reduced with DTT as described above. 0.5 gm of the isolated material was dissolved in deionized water at 10 % wt/vol. The pH of the solution was raised to 8.5 with NaOH. The solution was purged with air until it showed an increase in viscosity.

EXAMPLE 13

Oxidation of Thiol Containing Polymers

Polymer 10 was reduced with DTT as described above. 0.5 gm of the isolated material was dissolved in deionized water at 10 % wt/vol. The pH of the solution was raised to 8.5 with triethanolamine. To the solution a 1:1 mole ratio of DMSO to thiol was added. The solution was warmed to 50° C. and stirred until it showed an increase in viscosity.

EXAMPLE 14

Preparation of Modified Hydrophilic Polymers as Described in Example 5 and Determination of the Bioadhesive Capacity of the New Polymer Compositions Bioadhesion Testing: Simulated Gastric Fluid (SGF) and Simulated Intestinal Fluid (SIF) were made with certified ACS grade chemicals and deionized-distilled water. Polymer (0.20 g) pellets were pressed at 2 tons in a 13 mm KBr die. The pellets were affixed to the 13 mm(d)×41 mm(l) stainless steel probe using 3M Scotch Wallsaver removable poster tape, 19 mm wide. The edges of poster tape were held tightly to the shaft of the probe with 3M Outdoor Window Film Mounting tape, to add extra security.

All bioadhesion experiments were done at room temperature and at 1 atmosphere. A small stomach (pig) section (1½ inch×1½ inch) was soaked in SGF or SIF for 20 minutes. It was then carefully transferred to the test rig. The cell of the test rig was filled with 2.5 mL SGF or SIF at room temperature. The desired pellet was affixed to the probe and lowered into full cell, checking to be sure there were no air bubbles trapped under the pellet that would interfere with the contact area. Once clear, the test was run for six minutes at 0.5N force. Data was graphed and analyzed using the Texture Expert software.

The bioadhesion capacity of polymers of the present invention are shown below in gram second:

| Polymer | Polymer | Crosslinker | Bioadhesion Capacity (g s) |
|---|---|---|---|
| Polymer 5 | PAA/MAA | BAC | 865 |
| Polymer 8 | PAA | BAC | 241 |
| Polymer 15 | PMAA | Cystine | 138 |
| Polymer 12 | PAA | Cystamine | 170 |
| Polymer 18 | PAA | Cystine | 170 |
| Polymer 23 | Poly(allylamine) | diothiobis(succinimidyl propionate) | 106 |

The foregoing examples are illustrative embodiments of the invention and are merely exemplary. A person skilled in the art may make variations and modification without departing from the spirit and scope of the invention. All such modifications and variations are intended to be included within the scope of the invention as described in this specification and the appended claims.

What is claimed is:

1. A bioadhesive polymer having a bioadhesion capacity of at least 100 g s, the polymer being capable of degradation inside a mammal into discrete segments which are essentially non-degradable yet essentially excretable, the polymer being composed of polymer backbones and crosslinks bonding the polymer backbones to one another sufficiently so that the polymer is capable of forming a hydrogel in water, the polymer backbones having a molecular weight of less than 45,000 Daltons and a hydrodynamic radius of less than about 40 Angstroms and being composed of one or more polymerized or copolymerized monomer selected from the group consisting of allyl amine, acryl amine, amides, N-vinyl pyrrolidone, hydroxyethylmethacrylate, acrylic acid, methacrylic acid, maleic acid, salts of these acids and esters of these acids, maleic anhydride, $C_1$–$C_5$ alkyl vinyl ether and a neutral but hydrophilic comonomer, the crosslinks containing ester, peptide, disulfide or thiol links which are degradable in a mammal by enzymatic cleavage, exchange reactions with mucin, reduction or oxidation.

2. The polymer of claim 1, wherein the polymer backbones are composed of one or more polymerized or copolymerized monomers selected from the group consisting of acrylic acid. methacrylic acid, maleic anhydride, an allyl amine, an acryl amine and salts of acrylic acid and maleic acid.

3. The polymer of claim 2, wherein the polymer backbones are composed of one or more polymerized or copolymerized monomers selected from the group consisting of acrylic acid, methacrylic acid, maleic acid and salts thereof, and further wherein the crosslinks contain thiol or disulfide groups.

4. The polymer of claim 3, wherein the polymer backbones are further crosslinked with polyalkenyl polyether links.

5. The polymer of claim 3, further comprising at least one pharmaceutically active agent.

6. The polymer of claim 5, wherein the polymer backbone is crosslinked to the pharmaceutical agent by a crosslink which is degradable in a mammal.

7. The polymer of claim 4, further comprising at least one pharmaceutically active agent.

8. The polymer of claim 7, wherein the polymer backbone is crosslinked to the pharmaceutical agent by a crosslink which is degradable in a mammal.

9. The polymer of claim 1, further comprising at least one pharmaceutically active agent.

10. The polymer of claim 9, wherein the polymer backbone is crosslinked to the pharmaceutical agent by a crosslink which is degradable in a mammal.

11. The polymer of claim 1, wherein the polymer backbones are composed of polyallylamine.

12. A hydrogel comprising the polymer of claim 1 and water.

13. A hydrogel comprising the polymer of claim 2 and water.

14. A hydrogel comprising the polymer of claim 3 and water.

15. A hydrogel comprising the polymer of claim 9 and water.

* * * * *